(12) United States Patent  
Salky et al.

(10) Patent No.: US 8,597,310 B2  
(45) Date of Patent: Dec. 3, 2013

(54) LAPAROSCOPIC ANASTOMOSIS TOOLS AND TECHNIQUE

(75) Inventors: Barry A. Salky, New York, NY (US); Patrick N. Gutelius, Monroe, CT (US); Peter Wilson, Killingworth, CT (US); Mark James DeBisschop, Burlington, CT (US); Leo R. Mindick, Great Neck, NY (US)

(73) Assignee: Cook Medical Technologies LLC, Bloomington, IN (US)

( * ) Notice: Subject to any disclaimer, the term of this patent is extended or adjusted under 35 U.S.C. 154(b) by 258 days.

(21) Appl. No.: 12/955,120

(22) Filed: Nov. 29, 2010

(65) Prior Publication Data

US 2011/0077669 A1    Mar. 31, 2011

Related U.S. Application Data

(63) Continuation-in-part of application No. 12/351,399, filed on Jan. 9, 2009.

(51) Int. Cl.  
*A61B 17/04* (2006.01)

(52) U.S. Cl.  
USPC ............................ 606/148; 606/139; 606/151

(58) Field of Classification Search  
USPC .................. 606/157, 158, 148, 151, 153, 156  
See application file for complete search history.

(56) References Cited

U.S. PATENT DOCUMENTS

| | | | |
|---|---|---|---|
| 475,259 | A | 5/1892 | Turck |
| 669,034 | A | 2/1901 | Manly |
| 963,889 | A | 7/1910 | Kistler |
| 1,139,627 | A | 5/1915 | Baltzley |
| 1,865,453 | A | 7/1932 | Baltzley |
| 3,604,425 | A | 9/1971 | LeRoy |
| 4,332,060 | A | 6/1982 | Sato |
| 4,440,170 | A | 4/1984 | Golden et al. |
| 5,330,486 | A | 7/1994 | Wilk |
| 5,534,008 | A | 7/1996 | Acksel |
| 5,725,537 | A | 3/1998 | Green et al. |
| 5,766,189 | A * | 6/1998 | Matsuno ........................ 606/158 |
| 5,779,720 | A * | 7/1998 | Walder-Utz et al. .......... 606/151 |
| 5,896,624 | A | 4/1999 | Horswell |
| 7,305,741 | B2 | 12/2007 | Joe |

* cited by examiner

*Primary Examiner* — Gregory Anderson  
(74) *Attorney, Agent, or Firm* — Brinks Gilson & Lione

(57) ABSTRACT

An anastomosis normally closed clip comprising a first side including at least one first suture guide, the first suture guide being disposed on a top of the clip, the first end portion and the first suture guide defining a first suture space open toward the top of the clip, the first side further including a first carrier slot on the bottom of the clip; and a second side which is the mirror image of the first side. An introducer device is used to open the clip and introduce it into a patient over two organ segments to be sutured together and allow the clip to close. The suture spaces allow for continuous suturing of the organ segments. The introducer device is used to remove the clip from the patient after the suture procedure.

23 Claims, 17 Drawing Sheets

100

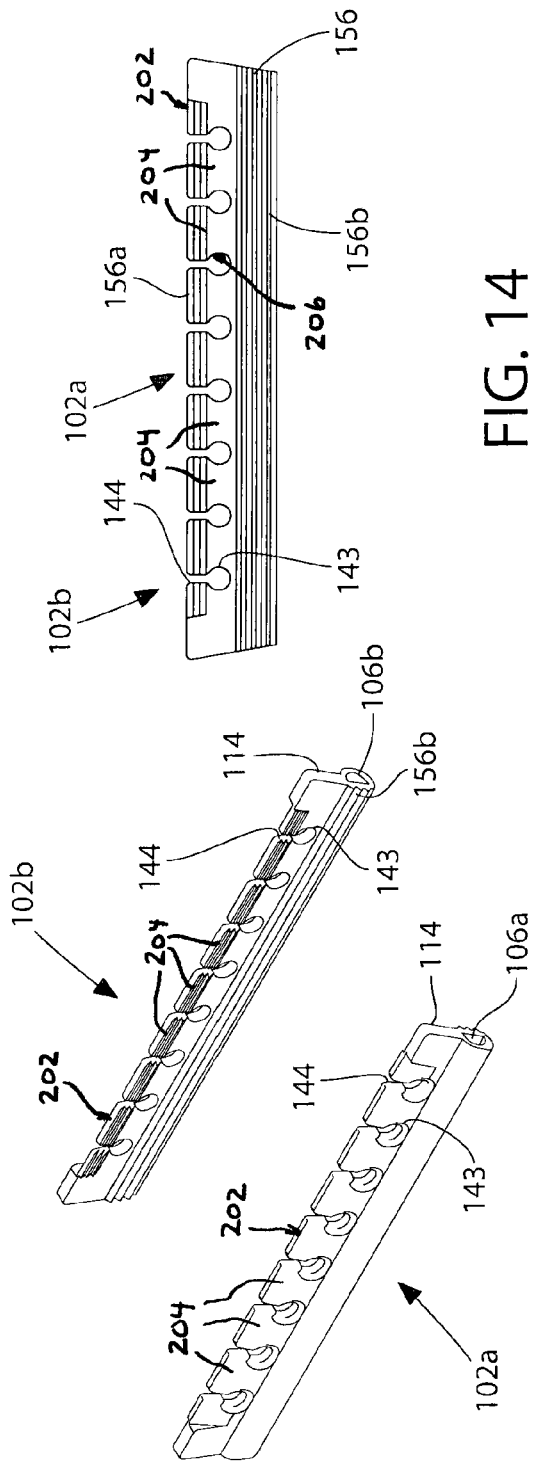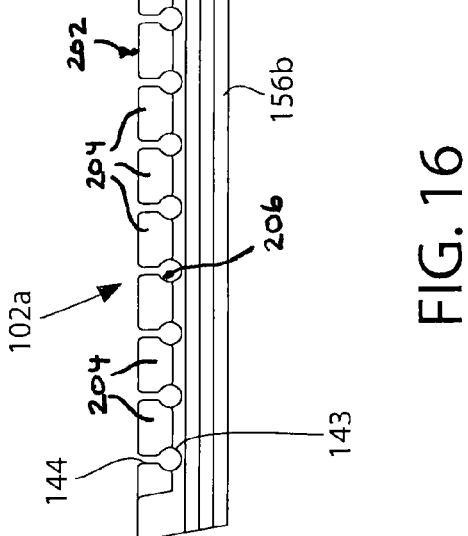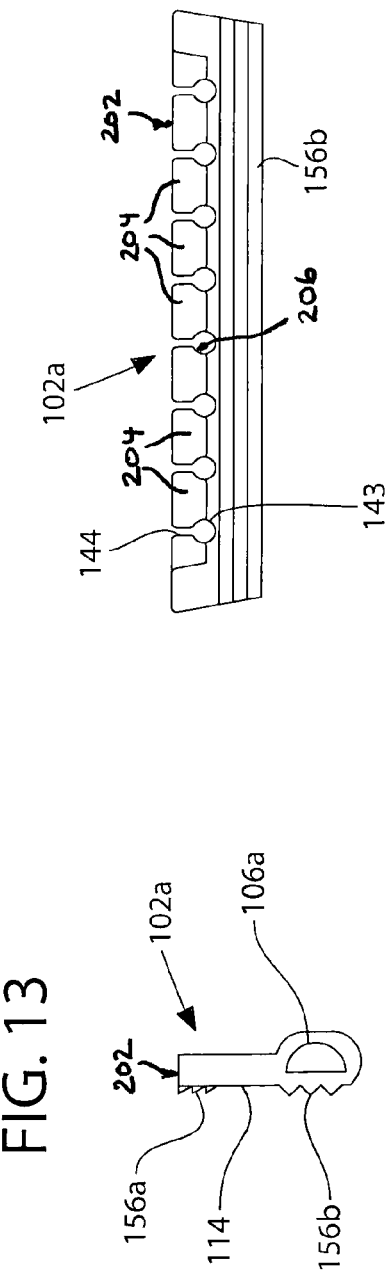

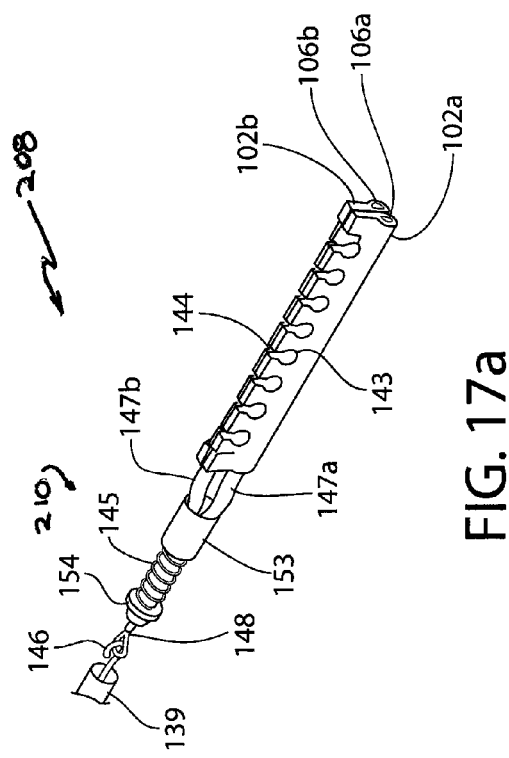
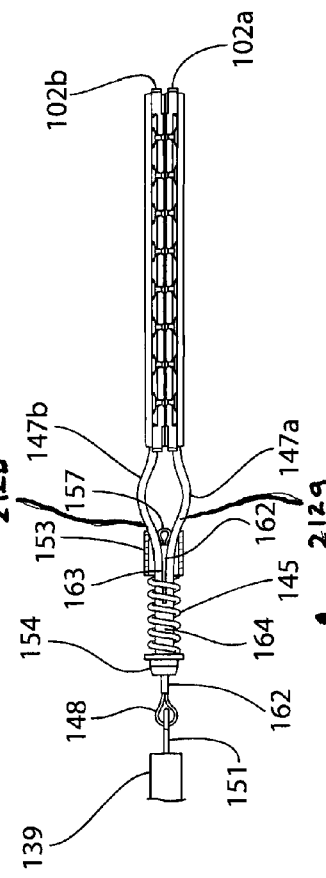
FIG. 17a
FIG. 17b

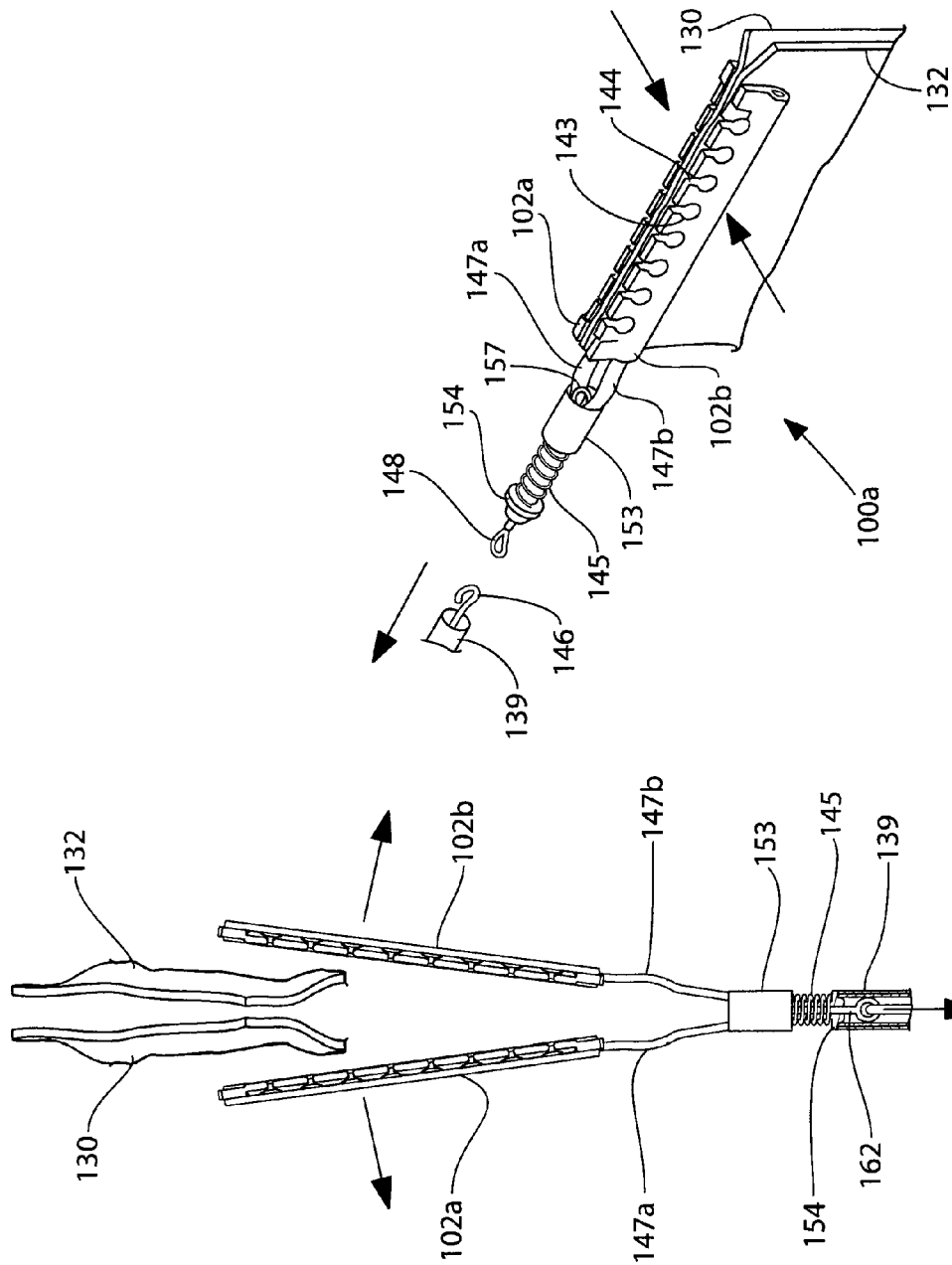

US 8,597,310 B2

LAPAROSCOPIC ANASTOMOSIS TOOLS AND TECHNIQUE

CROSS-REFERENCE TO RELATED APPLICATIONS

This application is a continuation-in-part of U.S. application Ser. No. 12/351,399, filed Jan. 9, 2009, the disclosure of which is incorporated by reference herein.

BACKGROUND OF THE INVENTION

This disclosure relates to laparoscopic anastomosis tools and techniques and, more particularly, to anastomosis tools and techniques that facilitate suturing.

An example of a prior art laparoscopic anastomosis technique 50 is described in U.S. Pat. No. 5,330,486—and is explained with reference to FIG. 1. In the shown technique, two organ segments 52, 54 are placed side-by-side and joined together. This joining may result in many benefits. For example, if a portion of the intestine is removed due to cancer, remaining portions of the intestine may be joined together using an anastomosis. In the example shown in FIG. 1, ends 56, 58 of the respective organ segments 52, 54, may be closed off. Connecting organ segment 52 with organ segment 54 may allow contents of organ segment 52 to flow through an opening 60 and into organ segment 54.

In order to perform the anastomosis technique, laparoscopic stapling members 62, 64 of respective laparoscopic stapling devices 66, 68, are inserted into organ segments 52, 54 via respective incisions or enterotomies 70, 72 formed in side walls of organ segments 52, 54. Laparoscopic stapling members 62, 64 are fixed to the ends of shafts 74, 76. The ends of shafts 74, 76 are adjustable by manipulating actuators 78, 80. Ends of shafts 74, 76 are inserted into a patient via respective trocar sleeves 82, 84 which traverse an abdominal wall 86.

Actuator 80 contains anastomosis staples and actuator 78 may contain an anvil member for assisting in the bending of the staple legs. A spindle 88 may be used to eject a threaded connector from actuator 80 into the anvil member. Actuator hand grips 90 are then squeezed to eject staples. Upon completion of the stapling operation, actuators 78, 80 are withdrawn from organ segments 52, 54 via enterotomies 70, 72. Enterotomies 70, 72 are then, in turn, closed.

Such prior art techniques have many problems. For example, by inserting stapling members 78, 80 through incisions 70, 72, additional suturing of incisions 70, 72 is necessitated. Moreover, these prior art techniques are limited to anastomosis using staples. However, stapling is not always the most desirable approach.

Performing an anastomosis using suturing instead of staples has advantages in many situations. At present, the majority of anastamoses are constructed outside the abdomen in laparoscopic surgery, because it is difficult for most surgeons to make the anastomosis intracorporeally. Laparoscopic assisted intestinal surgery involves mobilizing the intestine inside the abdomen, but an incision is made to extract the intestine from inside the abdomen and the anastomosis is completed through the extraction site. However, there is data to show that when an anastomosis is made intracorporeally, patients leave the hospital earlier, have less narcotic usage, have smaller extraction incisions, and have less complications when compared to extracorporeal laparoscopic assisted surgery.

SUMMARY OF THE INVENTION

It is therefore an object of the invention to provide new and improved tools and techniques for assisting surgeons in performing an anastaomosis.

Another object is to provide new and improved devices and methods of using the device for assisting a surgeon in suturing during surgery.

A further object is to provide new and improved tools and techniques for assisting a surgeon in placing sutures at uniform and appropriate distances from the edges of sectioned organs, and at uniform distances from each other.

These objects, and others which will become apparent from the following disclosure and drawings, are achieved by the present invention which comprises in one aspect an anastomosis clip comprising a first side and a second side, the first side including a first end portion and at least one first suture guide, the first end portion and the first suture guide defining a first suture space open toward a top of the clip, the first side further including a first carrier slot on the bottom of the clip, the second side including a second end portion and at least one second suture guide, the second end portion and the second suture guide defining a second suture space open toward the top of the clip, the second side further including a second carrier slot on the bottom of the clip. In some embodiments the clip further includes a hinge connecting the first and second side, the hinge being disposed on the top of the clip. The first side is biased toward the second side. In other embodiments the first side is distinct from the second side. In embodiments wherein the first side is distinct or separate from the second side, the first and second sides can be members of a clip assembly which includes means to maintain the first and second sides normally closed or biased toward each other.

In embodiments wherein the first side is distinct from the second side, each side can include a carrier slot adapted to receive a clamp arm which is not withdrawn from the slot during the suturing procedure. In these embodiments the clip can be a clip assembly which comprises two clamp arms which are fitted and fixed in respective carrier slots in the first side and second sides; a clamp arm actuator rod having a proximal end and a distal end, an eye on the proximal end of the clamp arm, a spread loop on the distal end of the clamp arm actuator rod, a collar guide on the clamp arm actuator rod between the eye and a spring, a sleeve on the distal end of the spring on the clamp arm actuator rod, the clip assembly configured so that when the clamp arm actuator rod is moved in a proximal direction against the resistance of the spring, the clamp arms spread apart. The clamp arms and the corresponding first side and second side of the assembly of this embodiment are normally urged or biased toward each other by action of the spring.

Another aspect of the invention is a method for suturing two organ segments, the method comprising providing an anastomosis clip comprising a first side and a second side, the first side including suture guides, defining a first suture space open toward a top of the clip, the first side further including a first carrier slot on the bottom of the clip and an introducer device, the second side including second suture guides, defining a second suture space open toward the top of the clip, the second side further including a second carrier slot on the bottom of the clip, manipulating the introducer device to introduce the clip over two patient organ segments; manipulating the introducer device to close the clip on the two organ segments; suturing the two organ segments together using the suture guides to guide the suturing, manipulating the introducer device to remove the clip from the sutures, opening the clip, and removing the clip from the sutured organ segments.

In some embodiments the introducer device comprises posts and the sides are hinged, and the method further comprises inserting the posts of the introducer into the first and second carrier slots of respective sides of the anastomosis clip; manipulating the introducer device to open the anastomosis clip; inserting the introducer device and anastomosis clip into a patient; and placing the anastomosis clip over two organ segments. The method further comprises manipulating the introducer device to close the anastomosis clip on the two organ segments; removing the introducer device from the patient; suturing the organ segments using suture guides in the anastomosis clip; and inserting the posts of the introducer device into the carrier slots of the anastomosis clip. The method further comprises manipulating the introducer device to open the anastomosis clip; lifting the introducer device and anastomosis clip off of the organ segments; and removing the introducer device and anastomosis clip from the patient.

In embodiments where the first and second sides are distinct and are members of a clip assembly, the method can comprise engaging an eye hook of an introducer device with the eye of the clip assembly, manipulating the introducer device for example by pulling a trigger to open the two sides, placing the open clip over two organ segments to be sutured, then releasing the trigger so that the two organ segments move toward each other. The operator then uses the suture spaces as targets for suturing, after which the introducer device is reengaged with the clip assembly, the clip assembly is moved in a downward direction, then opened and removed from the patient.

Another aspect of the invention is a combination of an anastomosis clip and an introducer device which is adapted to engage the clip at the start of a suture procedure to open the clip so it can be placed around two organ segments to be sutured, to close the clip, to move the clip away from the sutures, to open the clip again, and to disengage from the clip.

In the embodiments wherein the anastomosis clip comprises a hinge, the introducer device comprises a handle, and a first and a second posts which can be inserted in and removed from the carrier slots of the clip.

In embodiments where the first and second sides of the anastomosis clip are distinct, the introducer device can comprise means to engage a hook on a clip assembly and pull it in a proximal direction to open the clip, and returning the clip assembly to its normal closed position by allowing the hook to move in a distal direction.

In embodiments wherein the clamp arms are part of the clip assembly, the introducer can include a trigger, a tube, a cable within the tube, and an eye hook on the distal end of the cable. The introducer eye hook engages an eye on the proximal end of the clamp arm actuator rod and the trigger is used to move the cable proximally to withdraw the eye hook into the introducer tube cable. The introducer tube engages the collar guide and, upon further proximal motion of the introducer tube cable, the clamp arm actuator rod is also moved proximally and the spread loop on the distal end of the cable actuator rod engages the two clamp arms and spreads them apart, thereby opening the two sides of the anastomosis suture guide clip.

In other embodiments, alternative means to maintain the clamp arms normally closed are possible, and alternative means to spread the clamp arms in an open jaw-like fashion so that the two suture guide clips are also spread apart are possible. While the suture guide of the invention is especially useful in an anastomosis procedure intracorporeally, it can of course also be used in an extracorporeal laparoscopic and non-laparoscopic procedures.

BRIEF DESCRIPTION OF THE DRAWINGS

The drawings constitute a part of the specification and include exemplary embodiments of the present invention and illustrate various objects and features thereof.

FIG. 12a is side perspective view of an introducer device engaged with a clip assembly in accordance with another embodiment of the invention.

FIG. 12b is a top view of the introducer device and clip assembly of FIG. 12a.

FIG. 13 is a side perspective view of first and second sides of the clip assembly of FIG. 12 which are distinct.

FIG. 14 is a side elevation view of a side of the clip assembly of FIG. 12, illustrating ridges on the inside thereof.

FIG. 15 is a front view of the side of the clip assembly shown in FIG. 14.

FIG. 16 is a side elevation view of an alternative to the embodiment of the clip assembly side of FIG. 14 with a different ridge configuration.

FIG. 17a is a side perspective view of a clip assembly shown in FIG. 12 engaged to the hook of an introducer device.

FIG. 17b is a top view of the clip assembly of FIG. 17a with member 153 cut away.

FIG. 18a is a top view of a clip assembly of FIG. 12 being opened to spread apart the two sides and being introduced over two organ segments.

FIG. 18b is a side perspective view of the clip assembly of FIG. 18a wherein the two sides are closed upon two organ segments and the introducer device hook is disengaged from the clip assembly eye.

DETAILED DESCRIPTION OF THE PREFERRED EMBODIMENT(S)

Figure 1:
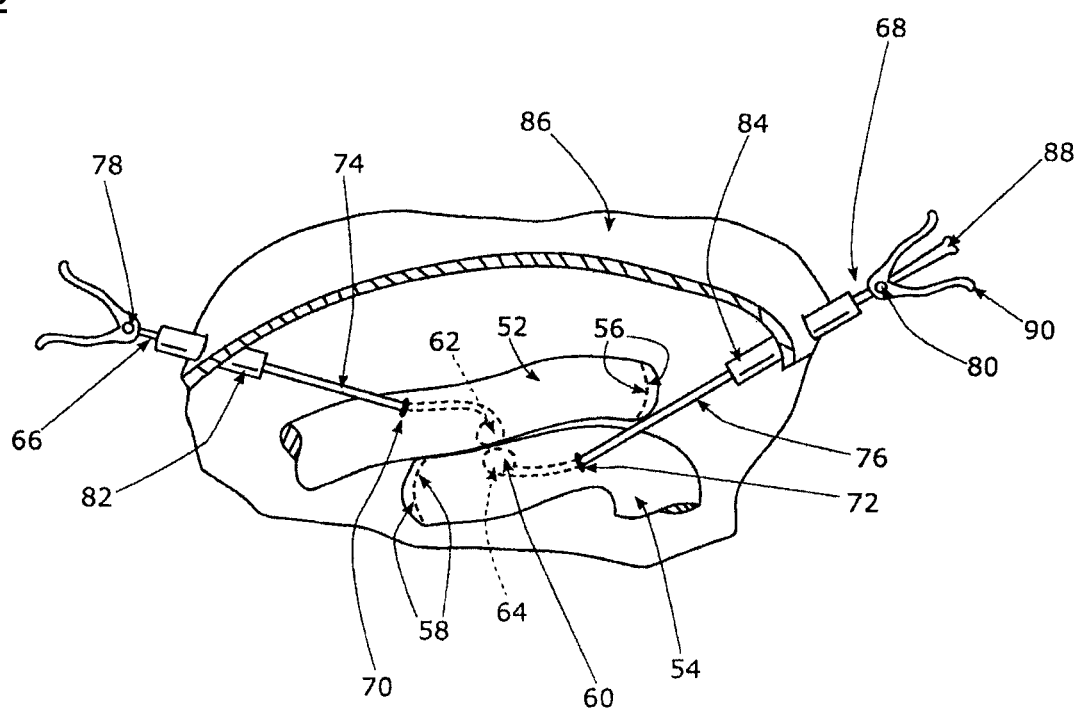
FIG. 1 is a front perspective cut-away view of an anastomosis technique in accordance with the prior art.

Various embodiments of the invention are described hereinafter with reference to the figures. Elements of like structures or function are represented with like reference numerals throughout the figures. The figures are only intended to facilitate the description of the invention and do not constitute a limitation on the scope of the invention. In addition, an aspect described in conjunction with a particular embodiment of the invention is not necessarily limited to that embodiment and can be practiced in conjunction with any other embodiments of the invention.

Figure 2:
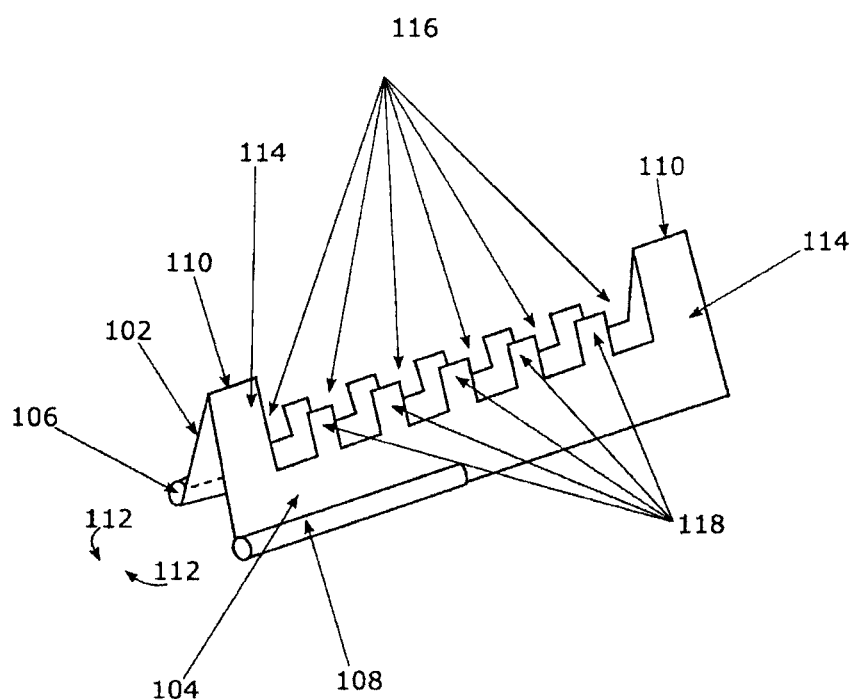
FIG. 2 is a perspective view of an anastomosis clip in accordance with an embodiment of the invention.

Referring now to FIG. 2, there is shown an anastomosis clip 100 in accordance with an embodiment of the invention. Clip 100 may be made of metal or plastic and could be made so as to be disposable. Clip 100 includes a first side 102 connected to a second side 104 by a hinge 110. First side 102 is biased closed toward second side 104 in the direction shown by direction arrows 112. Such a bias may be performed by a spring in hinge 110 or though the use of a material with a positional memory such as nitinol, though the use of a spring loaded plastic, or with any other known method or material. Sides 102, 104 include carrier slots 106, 108 respectively that may allow clip 100 to be used with an introducer device (discussed below). Sides 102 and 104 are symmetrical and so a discussion of one side effectively includes a discussion of the other. Focusing on side 104, side 104 includes end portions 114 that terminate in hinges 110 and side 104 includes suture guides 118 shown on a top of clip 100 though it should be clear that the terms top and bottom may be used interchangeably. End portions 114 and suture guides 118 define suture spaces 116 open toward the top of clip 100 and effective to allow for suturing of organ segments using clip 100.

Figure 3:
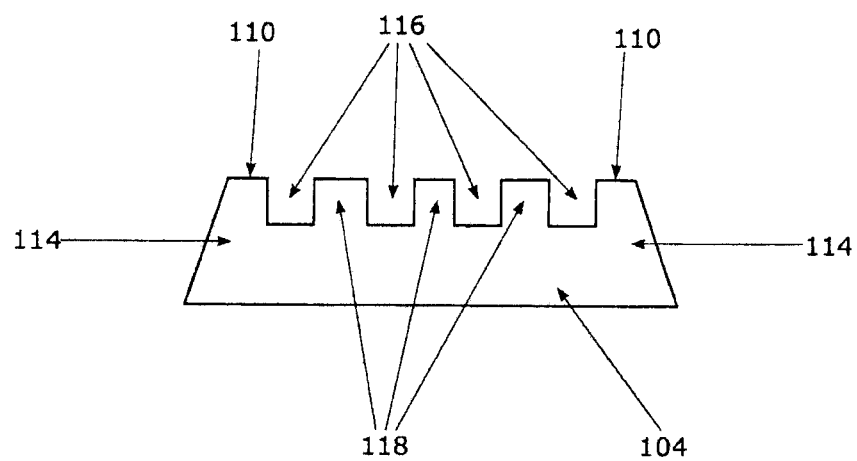
FIG. 3 is a side view of an anastomosis clip in accordance with an embodiment of the invention.
Figure 4:
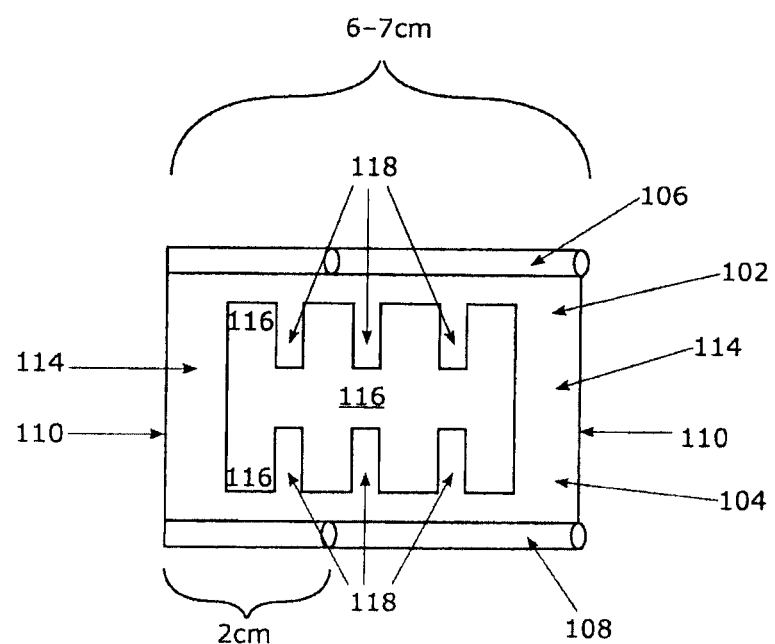
FIG. 4 is a top view of an open anastomosis clip in accordance with an embodiment of the invention.
Figure 5:
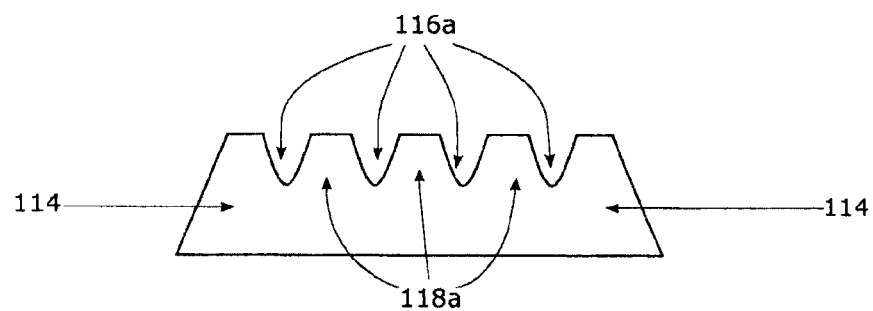
FIG. 5 is a side view of an anastomosis clip in accordance with an embodiment of the invention.

FIG. 2 shows five suture guides 118 though any number may be used. For example, as shown in FIG. 3, three suture guides 118 may be used. End portions 114 may taper outwardly. Suture guides 118 may have rectangular cross-sections as shown in FIGS. 2 and 3 and may extend inwardly as shown in FIG. 4 (where clip 100 is forced in an open position) to define suture spaces 116 having a fence shaped overall cross-section. As shown, suture spaces 116 on first side 102 communicate with suture spaces 116 on second side 104 because suture guides 118 on first side 102 do not meet with, i.e. are disconnected from, suture guides 118 on second side 104. Some potential dimensions for clip 110 are also shown—an overall length of the clip 100 may be 6-7 cm where 2 cm of the clip excludes carrier slots 106, 108. Clip 100 may also include suture guides defining arcuate suture spaces as shown in FIG. 5 with suture guides 118a and arcuate suture spaces 116a. Clearly, any shape of suture guide may be used to define any type of suture space.

Figure 6:
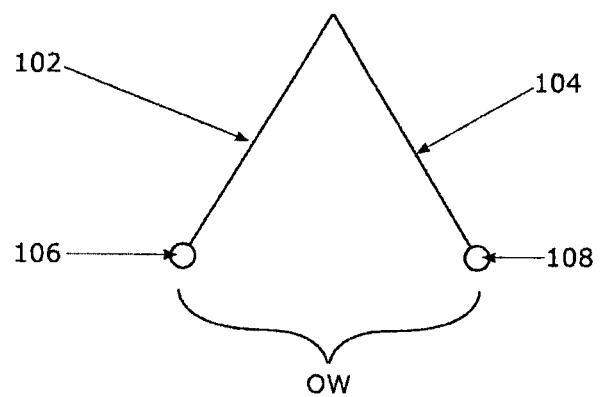
FIG. 6 is a front view of an open anastomosis clip in accordance with an embodiment of the invention.
Figure 7:
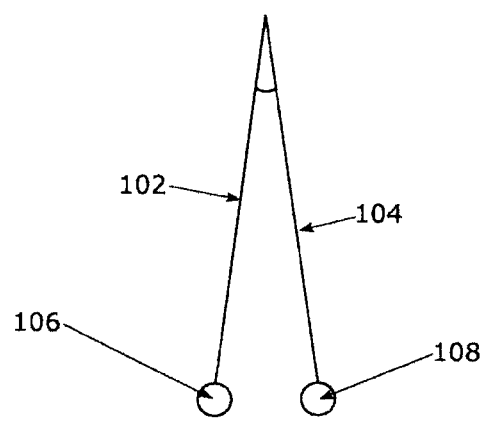
FIG. 7 is front view of a closed anastomosis clip in accordance with an embodiment of the invention.

Clip 100 is biased toward a closed position. When clip 100 is used in an anastomosis procedure, clip 100 is first forced to an open position as shown in FIG. 6. Clip 100 may be used in a laparoscopic procedure using a trocar (not shown). As a consequence, clip 100 may be designed so that in the open position, carrier slots 106, 108 define an opening width OW that is not greater than 11 mm so as to fit in a 12 mm diameter trocar. The portion of the jaw that holds the intestine can, in some embodiments, be about 5 mm tall to insure that the submucosal layer of the insestinal wall is incorporated into the sutures that will be placed through the target portion of the device, which can be the suture spaces 116, slits or slits terminating in bulls-eye shaped openings. Once clip 100 is in place around the organ segments, clip 100 is allowed to return to the closed position as shown in FIG. 7.

Figure 8:
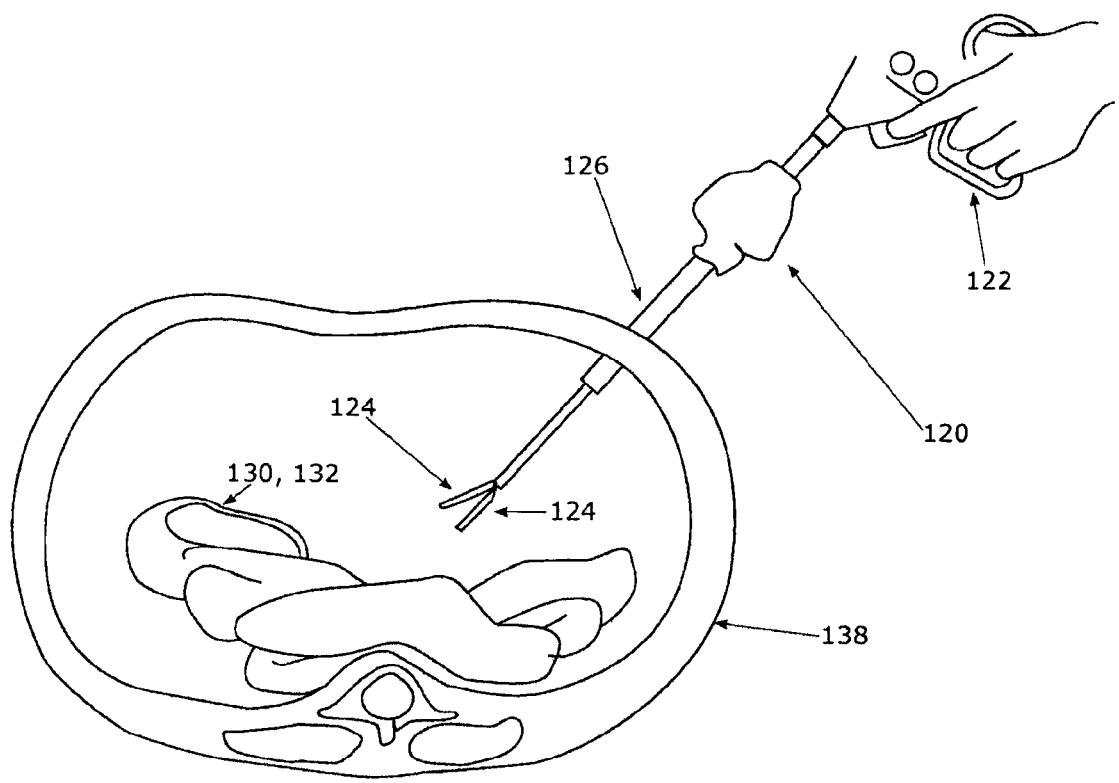
FIG. 8 is a top view of an open introducer device for introducing an anastomosis clip in accordance with an embodiment of the invention.
Figure 9:
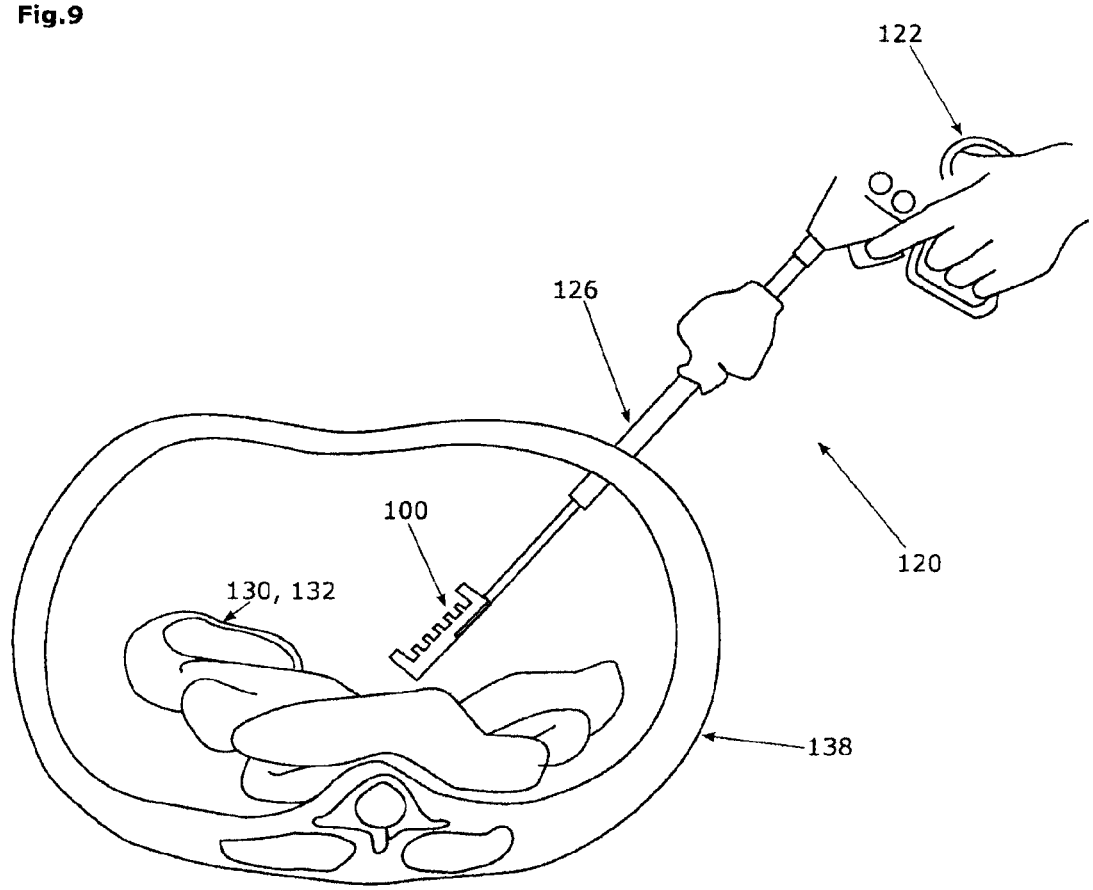
FIG. 9 is a top view of a closed introducer device for introducing an anastomosis clip in accordance with an embodiment of the invention.

If clip 100 is used in a laparoscopic procedure, the patient may be prepared for such procedure in accordance with known techniques in the art. For example, one or more trocars (not shown) may be inserted into the patient and used, in conjunction with a fiber optic camera, to allow access of clip 100 inside the patient. FIGS. 8 and 9 show an introducer device 120 which could be used to introduce clip 100 through a trocar in a laparoscopic procedure. Introducer device 120 may be made of, for example, plastic or metal. Introducer device 120 includes handles 122 and posts 124 connected by a hinge 126. Posts 124 may be inserted into carrier slots 106, 108 (FIG. 2) of clip 100 so that introducer device 120 can introduce clip 100 into a patient.

Manipulation of handles 122 inward and outward causes movement of posts 124. For example, a squeezing of handles 122 toward one another may result in an opening or spreading apart of posts 124 as shown in FIG. 8. Conversely, a spreading of handles 122 may result in a closing of posts 124 as shown in FIG. 9. Handles 122 and posts 124 may be naturally biased toward a position where posts 124 are closed, such as, for example, using a spring to bias handles 122 in an open position, through the use of nitinol, a spring biased plastic or any other known method.

For example, focusing on FIGS. 2, 8 and 9, as discussed above, clip 100 may be biased toward a closed position and posts 124 of introducer 120 may be biased toward a closed position. A user may insert posts 124 into carrier slots 106, 108. The user may then squeeze handles 122 causing posts 124 and carrier slots 106, 108 to open (see FIGS. 6 and 8). As opening width OW (FIG. 6) of clip 100 may be 11 mm, introducer 120 and clip 100 may be inserted into a 12 mm diameter trocar even while clip 100 is in an open position.

Figure 10:
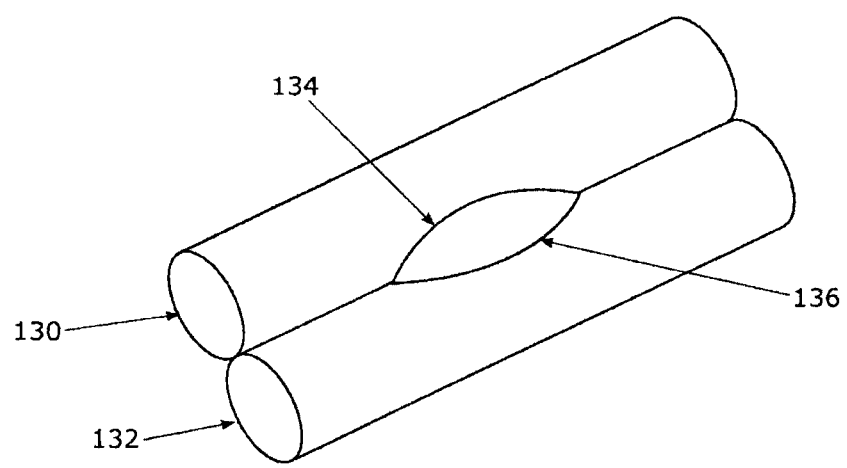
FIG. 10 is a front perspective view of two organ segments.
Figure 11:
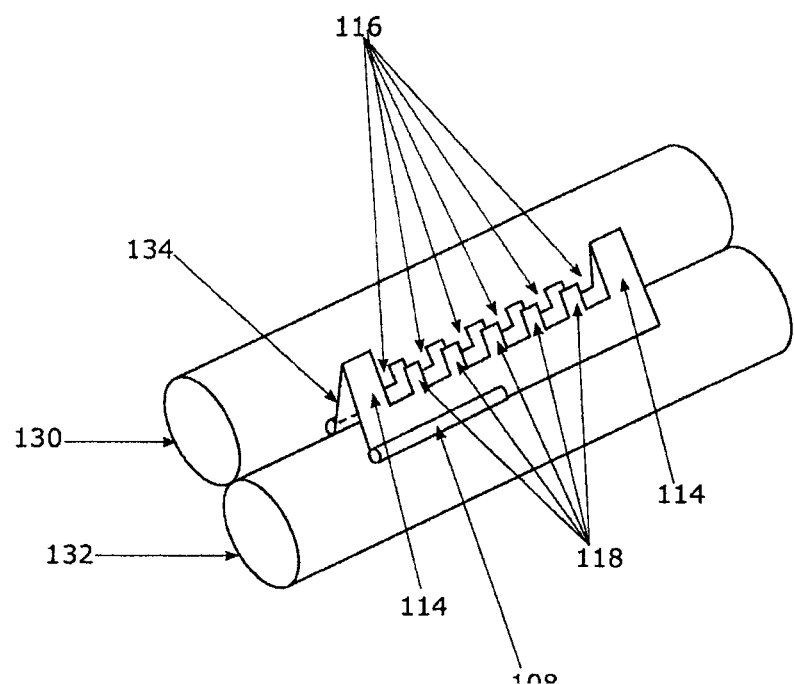
FIG. 11 is a front perspective view of two organ segments and an anastomosis clip in accordance with an embodiment of the invention.
Figures 12A, 12B:
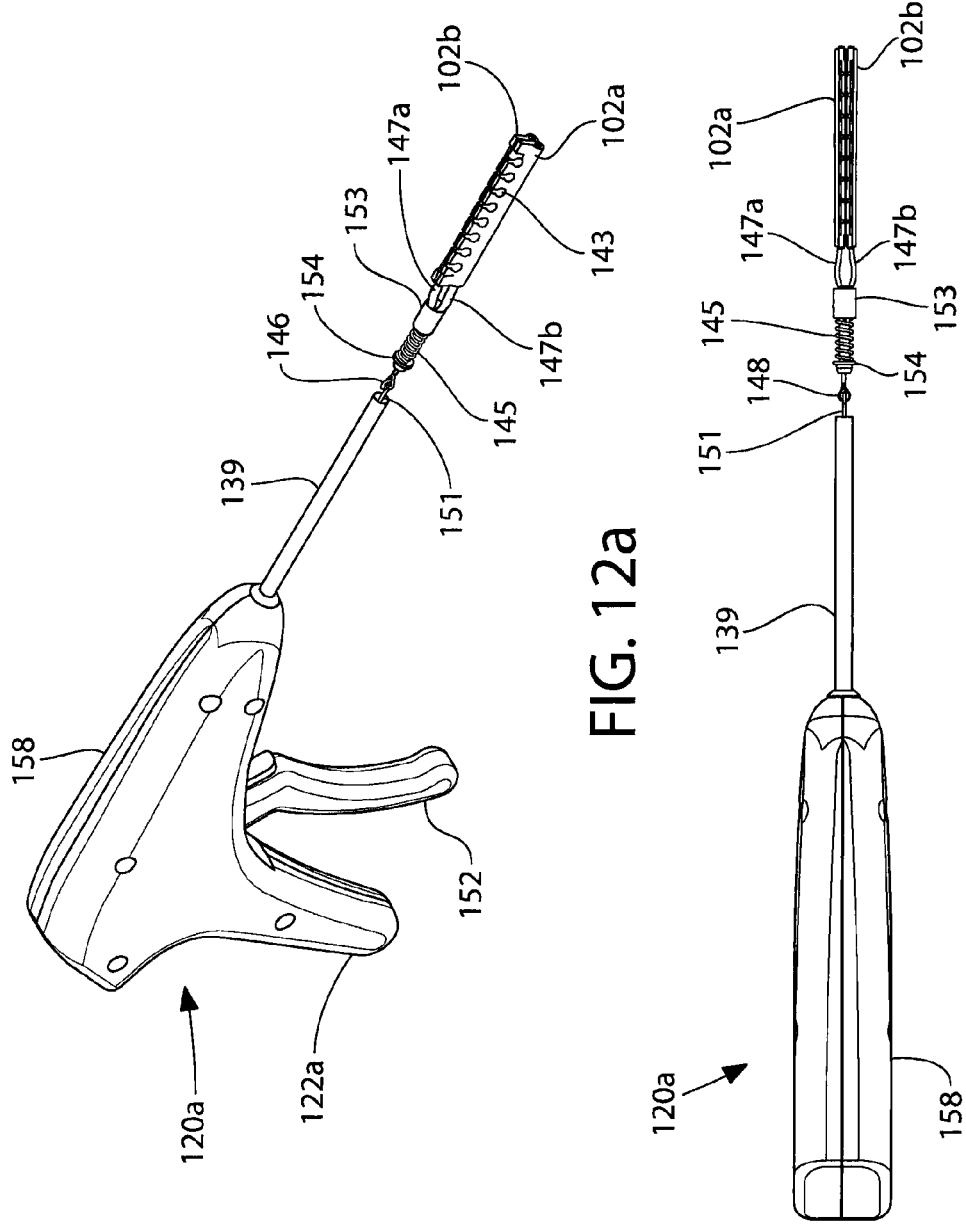

FIG. 10 shows two organ segments 130, 132 placed side by side to one another. First and second sides 134, 136 of an opening are shown and it is desirable to suture sides 134, 136 together. Clip 100 may be used to facilitate such suturing. With posts 124 of introducer 120 forcing clip 100 open, clip 100 is placed over organ segments 130, 132 as shown in FIG. 11. Once clip 100 is in a desired position, a user may allow introducer 120 to close, thereby closing clip 100 on organ segments 130, 132 due to the bias of first side 102 toward seconds side 104. Introducer 120 may then be removed from the patient while clip 100 remains.

As discussed above, clip 100 includes suture spaces 116 defined by suture guides 118. Suture spaces 116 are designed to facilitate suturing or laparoscopic suturing. For example, clip 100 can line up organ segments 130, 132 so that a continuous suture can be applied. Prior art laparoscopic suturing is difficult because of, in part, the difficulties in lining up two ends of organ segments together to enable proper placement of needles for sutures. Clip 100 helps solve that problem by effectively lining up organ segments 130, 132, and holding organ segments 130, 132 next to one another while defining suture spaces 116 for suturing.

As shown in FIG. 11 and also in FIG. 4, as suture guides 118 on first side 102 do not meet with suture guides 118 on second side 104, a top of clip 100 is generally open because respective suture spaces 116 on sides 102, 104 communicate and both are open toward the top of clip 100. This means that sutures may be placed through suture spaces 116 and clip 100 may thereafter be lifted upward and removed from organ segments 130, 132. For example, after sutures (not shown) are used to suture opening 134, 136, introducer 120 may be reinserted into the patient and posts reinserted into carrier slots 106a, 106b. Handles 122 of introducer 120 are then squeezed to open posts 124, carrier slots 106, 108 and clip 100. Clip 100 may then be lifted off of organ segments 130, 132 and removed from a patient. Such a technique could be performed through a trocar or through traditional open surgery methods.

Referring now to FIGS. 12-20, an embodiment of the invention in which the sides of the anastomosis clip are distinct or separate from each other is illustrated. FIGS. 12*a* and 12*b* illustrate an embodiment of an introducer 120*a* engaged via eye hook 146 to an eye 148 of a clip assembly. The clip assembly has a first, left side 102*a* and a distinct or separate second, right side 102*b* and left and right clamp arms 147*a* and 147*b* fixed within carrier slots 106*a* and 106*b* (FIG. 13). The introducer 120*a* has a housing 158, a handle 122*a*, a trigger 152, a tube 139, and a cable 151 within the tube 139 which includes a hook 146 adapted to engage with or disengage from eye 148 of the clip assembly. Referring to FIG. 17*b*, the clip assembly includes a clamp arm actuator rod 162 which connects eye 148 on its proximal end to spread loop 157 on its distal end and is surrounded by spring 145, sleeve 153, and stainless steel collar guide 154.

The first and second sides are shown in more detail in FIG. 13. Each side 102*a*, 102*b* is preferably formed of molded plastic and comprises an elongate member having an upper edge surface 202 and a plurality of suture guides 204 defining a corresponding number of suture spaces 206 (FIG. 14) between them. Each suture space 206 includes a substantially circular opening or bulls-eye 143 and a slit 144 extending from the top of the bulls-eye 143 and opening onto the upper edge surface 202 of the side 102*a*, 102*b*. The centers of the bulls-eyes 143 are uniformly situated between 0.10" and 0.20" from the upper edge surface 202, preferably about 0.125", and uniformly between about 0.20" and 0.30" from each other, preferably about 0.25". Each side in the illustrated embodiment is about 2.3" long, 0.35" high, about 0.060" at the top and about 0.10" thick at the bottom which includes a D-shaped channel for receiving the clamp arms constituted by respective carrier slots 106*a* and 106*b* extending along their lower edge portions.

As best seen in FIG. 14 each of the sides 102*a* and 102*b* have elongate, longitudinally extending, parallel serrations or ridges 156, which face the opposing side. The lower portion of the side has ridges 156*b* of a close configuration and the upper portion of each side, 102*a*, 102*b*, has ridges 156*a* of a wider spaced configuration, although any combination of ridges such as that illustrated in FIG. 16, or other rough surfaces such as incorporating tongues and grooves can be used in order to assist in securing two organ parts to each other during a suturing procedure.

FIG. 15 shows a side view of side 102*a*, showing top ridges 156*a* and bottom ridges 156*b*, with a D-shaped carrier slot 106*a*.

FIGS. 17*a* and 17*b* illustrate the clip assembly of FIG. 12. The clip assembly, generally designated 208, comprises the clip sides 102*a* and 102*b* and biasing means 210 which are coupled to clip sides 102*a* and 102*b* which urge the clip sides 102*a* and 102*b* toward each other. Whereas the biasing means in the case of the embodiments shown in FIGS. 1-11, are constituted by the hinges 110 coupled to the end portions 114 of sides 102 and 104, the biasing means of the clip assembly 208 of FIGS. 12-20 are constituted by a clamping assembly including a tubular portion 164 which is bifurcated at its distal end from which a pair of clamp arms 147*a* and 147*b* extend. The clamp arms 147*a*, 147*b* include cam portions 212*a*, 212*b* which diverge from each other in the distal direction and which then converge and terminate in clamp arm coupling portions (not shown) which are situated in carrier slots 106*a* and 106*b* of clip sides 102*a*, 102*b*. An actuator rod 162 is situated within the tubular portion 164 and is freely movable therein. An eye 148 is connected to the proximal end of the actuator rod 162 and a spread loop 157 is connected to the distal end of the actuator rod 162. A cylindrical sleeve 153 surrounds the proximal ends of the clamp arms 147*a*, 147*b* and has a distal end that engages the cam portions 212*a*, 212*b* of clamp arms 147*a*, 147*b*. A compression spring 145 surrounds the tubular portion 164 of the clamping assembly and its distal end bears against the proximal end of cylindrical sleeve 153. A collar guide 154 is threadedly affixed to the proximal end of tubular portion 164 and bears against the proximal end of spring 145. The spring is normally compressed so as to urge the cylindrical sleeve in a distal direction over the cam portions 212*a*, 212*b* of clamp arms 147*a*, 147*b* to urge the sides 102*a*, 102*b* inwardly towards and into engagement (assuming no organ wall is situated between the sides) with each other (the "closed" position).

The force with which the sides 102*a*, 102*b* press against each other can be adjusted by adjusting the position of the collar guide 154 on tubular portion 164.

When the clip sides 102*a*, 102*b* are in their closed position as seen in FIGS. 17, 17*b* and 18*b*, the bulls-eyes 143 and slits 144 in the respective sides are aligned with each other.

The introducer 120*a* functions as an actuation device to open the clip assembly, i.e., move the clip sides 102*a* and 102*b* apart and away from each other so that the clip can be placed on organ segments 130 and 132. In particular, the hook 146 attached to the end of the cable 151 is coupled to the eye 148 attached to the actuator rod 162. When the trigger 152 of the introducer is squeezed, the cable 151 is retracted in the proximal direction into the introducer tube 139. As seen in FIGS. 18*a* and 18*b*, the collar guide 154 is pulled in the proximal direction until it engages the end of the introducer tube 139. Continued retraction of cable 151 continues to pull the actuator rod 162 in the proximal direction causing the spread loop 157 to move in the proximal direction in the V-shaped space defined between the cam portions 212*a*, 212*b* of the clamp arms 147*a*, 147*b* thereby urging the clamp arms, and sides coupled thereto, away from each other to open the clip. As seen in FIG. 18*a*, the sleeve 153 is moved by the opening movement of the cam portions 212*a,b* in a proximal direction and compresses the spring 145.

FIG. 18*a* shows clamp arms 147*a* and 147*b* being opened and in turn opening the clip consisting of sides 102*a* and 102*b* so that the clip can be placed on organ segments 130 and 132. The clip is opened due to the tension being applied by the introducer device which is moving eye 148 (shown in FIG. 18*b*) proximally while introducer device tube 139 engages collar guide 154.

In FIG. 18*b*, the clip is illustrated as being closed on organ segments 130 and 132 and the introducer device being unhooked and withdrawn. The bulls-eyes 143 and slits 144 on each of the sides 102*a*, 102*b* are aligned with each other.

Figure 19:
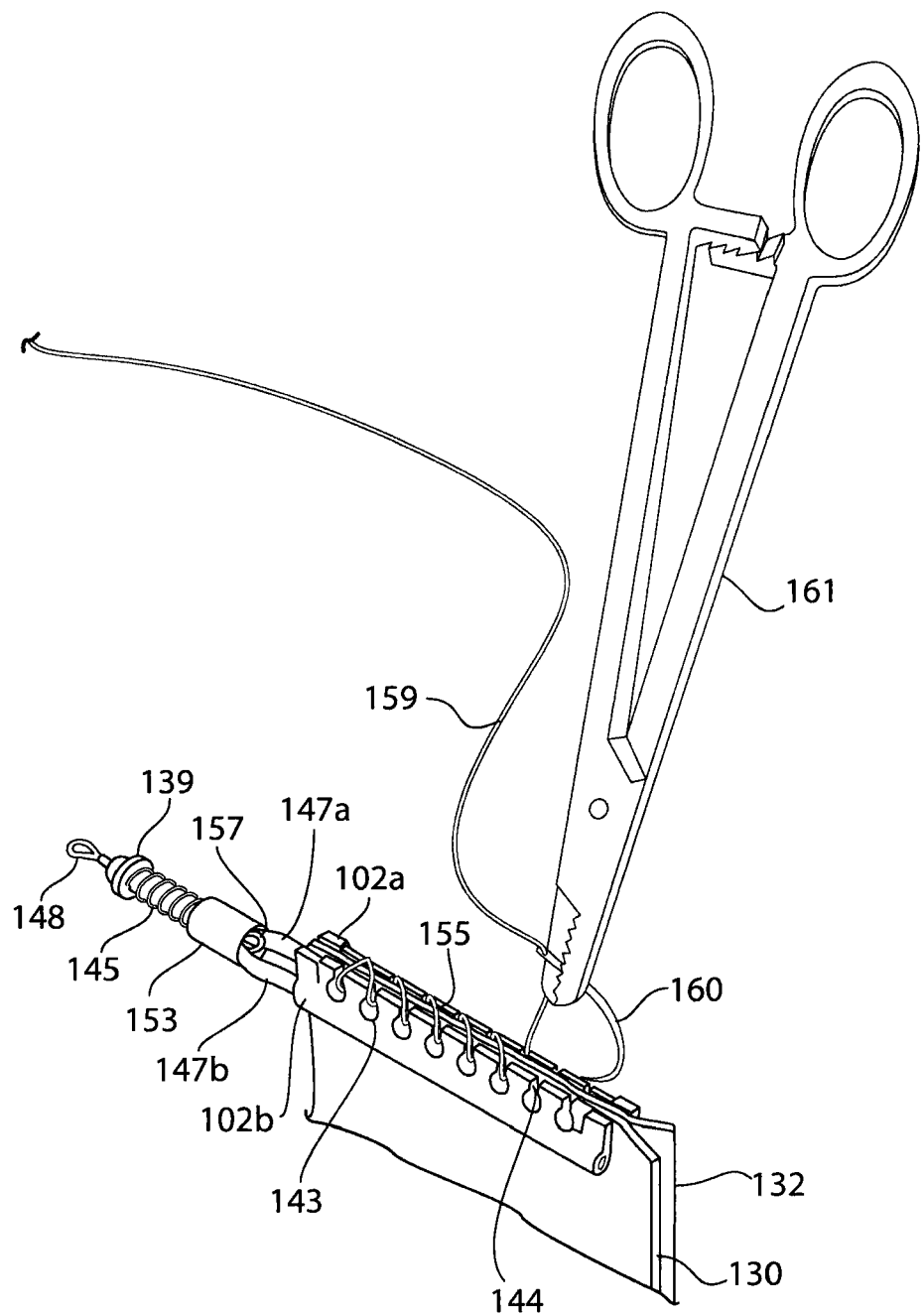
FIG. 19 is a side perspective view of a clip assembly in accordance with the embodiment of FIG. 12 closed upon two organ segments and being used to guide a suture procedure.

FIG. 19 shows the clip assembly holding the organ segments 130 and 132 together while forceps 161 engage suture needle 160 to suture the organ segments through the bulls-eyes 143 of the sides 102*b* and 102*a*. The clip assembly is preferably not engaged at this point with the introducer device. The sides 102*a*, 102*b* of the clip compress the organ segments between them under the force of the compressed spring 145. The serrations or ridges 156 on the opposed clip sides bite into the organ segments and tend to prevent slippage.

Figure 20:
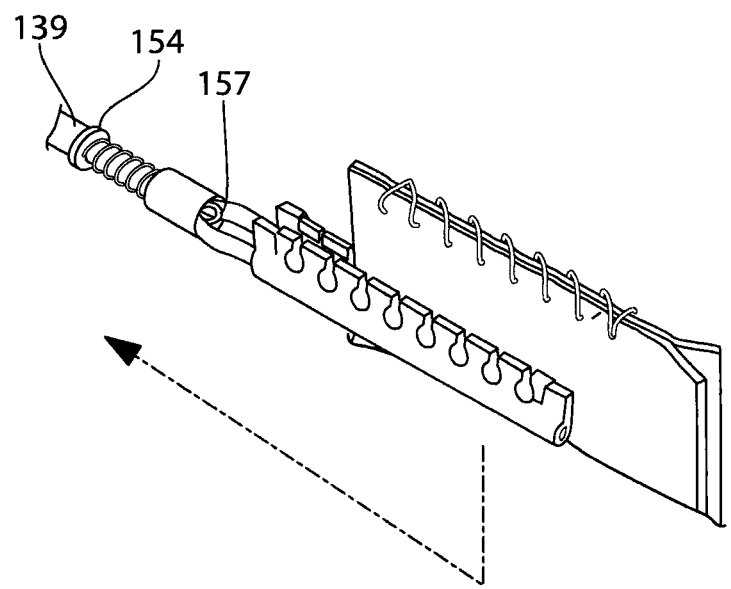
FIG. 20 is a side perspective view of a clip assembly in accordance with the embodiment of FIG. 12 being removed from two organ segments having been sutured according to the invention, leaving the sutures intact.

FIG. 20 illustrates the eye of the clip being reengaged with the hook of the introducer device, the clip being slightly opened so that it can be moved down without disturbing the sutures, and then opened and withdrawn in the direction of the arrow. The sutures pass from the bulls-eyes 143 through the slits 144 as the clip is removed.

Thus, when the trigger 152 is pulled and the suture guide clips are in turn caused to spread apart, the suture guide clip assembly, called the "Anastomiotic Intracorporeal Device Enabler" (A.I.D.E.), is placed intracorporeally over two organ parts to be sutured, for example stomach and small intestine, two pieces of small intestine, small intestine and large intestine (colon), or two pieces of colon. A trocar (not shown) may be used during this step. The trigger is then released, causing the cable 151 within the tube 139 to move distally and the pressure caused by the tube against the stainless steel collar guide 154 to be released which in turn causes the spring to press against sleeve 153 to close the clamp arms toward each other and urge the two suture guide clip sides 102a and 102b toward each other, thereby pressing the two pieces of, for example, small intestine, to each.

The device of the invention assists the surgeon in making an anastomosis inside the body, i.e., intracorporeally, which has great advantages in the field of gastrointestinal surgery, allowing patients to leave a hospital earlier than with an extracorporeal anastomosis. A smaller incision is used with an intracorporeal anastomosis, which is also an advantage afforded by the apparatus and method of the invention.

Further, the clip includes guides to facilitate the suturing—a difficult process if using prior art devices devoid of such guides. The invention has been described with reference to an embodiment that illustrates the principles of the invention and is not meant to limit the scope of the invention. Modifications and alterations may occur to others upon reading and understanding the preceding detailed description. It is intended that the scope of the invention be construed as including all modifications and alterations that may occur to others upon reading and understanding the preceding detailed description insofar as they come within the scope of the following claims or equivalents thereof. Various changes may be made without departing from the spirit and scope of the invention.

While the invention is shown in use in connection with an intracorporeal laparoscopic anastomosis, it will be understood that the invention be not so limited. For example, the invention may be used in connection with an extracorporeal laparoscopic procedure or a non-laparoscopic procedure.

What is claimed is:

1. An anastomosis clip comprising:
    a first side including a first end portion and at least one first suture guide, the first end portion and the first suture guide defining a first suture space open toward a top of the clip, the first side further including a first carrier slot on the bottom of the clip;
    a second side, including a second end portion and at least one second suture guide, the second end portion and the second suture guide defining a second suture space open toward the top of the clip, the second side further including a second carrier slot on the bottom of the clip;
    wherein the first side and the second side are distinct from each other and
    wherein the first side is biased toward the second side and the first and second sides are configured to receive tissue therebetween; and
    wherein the first and second suture spaces are configured to receive a suture from the top of the clip.

2. The clip as recited in claim 1, wherein the first and second suture guides have a rectangular cross-section.

3. The clip as recited in claim 1, wherein the first and second suture spaces are arcuate.

4. The clip as recited in claim 1, wherein the sides are between about 7 and 11 mm tall, about 4.5 to 5.0 cm long.

5. The clip as recited in claim 1, wherein the first suture guide is distinct from the second suture guide.

6. The clip as recited in claim 1, further comprising a hinge connecting the first and second side.

7. The clip as recited in claim 6, wherein the first suture space communicates with the second suture space.

8. The clip as recited in claim 6, wherein the hinge biases the first side toward the second side.

9. The clip as recited in claim 1 wherein the clip is an assembly comprising a first and second clamp arms engaged within the first and second carrier slots, respectively, and means to urge the first and second clamp arms normally toward each other and thereby close the clip so that the first and second suture spaces of the first and second sides, respectively, are aligned.

10. The clip of claim 9 wherein the means to urge the first and second suture guides together comprises a spring and the means to urge the first and second suture guides away from each other comprises means to spread the clamp arms.

11. The clip of claim 9 comprising means to open the clip by urging the first and second sides away from each other during insertion and engagement of tissue segments and during removal of the apparatus from the tissue segments.

12. The clip of claim 11 wherein the means to open the clip by urging the first and second sides away from each other comprises a mechanism to spread the clamp arms which comprises a clamp arm actuator rod comprising an eye on a proximal end and a spread loop on a distal end.

13. A combination of an anastomosis clip according to claim 1 and an introducer device, the introducer device comprising a handle, means to engage the clip, means to open the clip, means to allow the clip to close, and means to disengage the clip.

14. The apparatus of claim 13 wherein the introducer device comprises a trigger, shaft, housing, cable having a distal end within the shaft, and an eye hook on the distal end of the cable.

15. The combination of claim 13 wherein the introducer device comprises a first hinge connected to the handle, and a first and a second post connected to the first hinge.

16. The combination of claim 13 wherein the introducer device comprises a housing, a trigger, a handle, a tube, a cable within the tube, the cable having a distal end and a hooking means at the distal end.

17. The combination of claim 16 wherein the clip is an assembly comprising first and second clamp arms engaged within the first and second carrier slots, respectively, further including means to spread the clamp arms and thereby urge the first and second clamp arms away from each other comprising a clamp arm actuator rod having a proximal end and an eye on the proximal end, and a distal end having a spread loop, arranged so that when the clamp arm actuator rod is moved proximally by the introducer, the clip is opened.

18. The clip of claim 1 wherein the first side comprises a pair of first end portions and a plurality of adjacent first suture guides between the pair of first end portions, the plurality of first suture guides defining a plurality of first suture spaces, and wherein the second side comprises a pair of second end portions and a plurality of adjacent second suture guides between the pair of second end portions, the plurality of second suture guides defining a plurality of second suture spaces.

19. A method comprising
    engaging an anastomosis clip according to claim 1 with an introducer device;
    manipulating the introducer device to open the clip;
    introducing the open clip into a patient;
    placing the first and second sides over two organ segments;
    manipulating the introducer device to close the first and second sides on the two organ segments;
    removing the introducer device from the patient;

suturing the organ segments using suture spaces in the anastomosis clip;
connecting the introducer device to the anastomosis clip;
manipulating the introducer device to open the anastomosis clip;
removing the anastomosis clip from the organ segments without disturbing the sutures; and
removing the introducer device and anastomosis clip from the patient.

20. The method of claim 19 comprising: inserting posts of an introducer device into carrier slots of an anastomosis clip; and manipulating the introducer device to open the anastomosis clip; inserting the introducer device and anastomosis clip into a patient.

21. The method of claim 19 wherein the clip is an assembly comprising a first and second clamp arms engaged within the first and second carrier slots, respectively, a clamp arm actuator rod having a proximal end and an eye on the proximal end and a distal end having a spread loop, moving the clamp arm actuator rod proximally with the introducer to open the clip and allowing the clamp arm actuator rod to move distally to close the clip.

22. The method of claim 19, wherein the inserting the introducer device, suturing, and removing the introducer device are performed through a trocar.

23. The method of claim 19 wherein the step of suturing the organ segments comprises applying a continuous suture to the organ segments from the top of the clip.

* * * * *